(12) United States Patent
Rahko et al.

(10) Patent No.: US 9,330,238 B2
(45) Date of Patent: May 3, 2016

(54) PERFORMANCE INTENSITY ZONES

(71) Applicant: Polar Electro Oy, Kempele (FI)

(72) Inventors: Juho Rahko, Kempele (FI); Hannu Kinnunen, Kempele (FI); Harri Maatta, Kempele (FI); Jarkko Haataja, Kempele (FI); Tanja Kalliojarvi, Kempele (FI); Ville Peltola, Kempele (FI)

(73) Assignee: POLAR ELECTRO OY, Kempele (FI)

( * ) Notice: Subject to any disclaimer, the term of this patent is extended or adjusted under 35 U.S.C. 154(b) by 149 days.

(21) Appl. No.: 13/665,022

(22) Filed: Oct. 31, 2012

(65) Prior Publication Data

US 2013/0110265 A1  May 2, 2013

(30) Foreign Application Priority Data

Nov. 1, 2011  (FI) ..................................... 20116072

(51) Int. Cl.
*A63B 71/00* (2006.01)
*A63B 15/02* (2006.01)
*G06F 19/00* (2011.01)

(52) U.S. Cl.
CPC .................. *G06F 19/3481* (2013.01)

(58) Field of Classification Search
USPC ........................................................ 482/6–9
See application file for complete search history.

(56) References Cited

U.S. PATENT DOCUMENTS

| 4,625,733 | A | 12/1986 | Saynajakangas |
| 6,882,955 | B1 | 4/2005 | Ohlenbusch et al. |
| 2008/0300498 | A1* | 12/2008 | Edwards ....................... 600/520 |
| 2010/0292599 | A1* | 11/2010 | Oleson et al. ................. 600/519 |
| 2012/0015779 | A1* | 1/2012 | Powch et al. ...................... 482/9 |

FOREIGN PATENT DOCUMENTS

| EP | 1178374 | A2 | 2/2002 |
| EP | 2239023 | A1 | 10/2010 |
| EP | 2260910 | A1 | 12/2010 |
| EP | 2320317 | A1 | 5/2011 |

OTHER PUBLICATIONS

"Polar Listen to Your Body," Help Section of the Polar Protrainer 5 Version Software 4.41.000 published Dec. 18, 2012, pp. 1-190.
(Continued)

*Primary Examiner* — Stephen Crow
*Assistant Examiner* — Shila Jalalzadeh Abyane
(74) *Attorney, Agent, or Firm* — Hoffmann & Baron, LLP (57) ABSTRACT

Performance intensity zones are disclosed. An apparatus comprises one or more processors, and one or more memories storing instructions, that, when executed by the one or more processors, cause the apparatus to: obtain performance intensity data measured from a user with at least one measurement sensor during a first activity and/or a second activity; and classify the performance intensity data in relation to a plurality of predetermined performance intensity zones, wherein each performance intensity zone is predetermined by a first numerical range for the first activity, and a second numerical range for the second activity, wherein the first activity and the second activity are different types of sports or different types of physical activities.

12 Claims, 4 Drawing Sheets

(56) References Cited

OTHER PUBLICATIONS

Search Report for Finnish Priority Application No. 20116072, dated May 22, 2012, pp. 1.

European Search Report for corresponding European Application No. EP10004889, 2 pages, Nov. 4, 2010.

* cited by examiner

PERFORMANCE INTENSITY ZONES

CROSS-REFERENCE TO RELATED APPLICATION

This application claims priority to Finnish Patent Application No. 20116072, filed Nov. 1, 2011, which is incorporated by reference herein in its entirety.

BACKGROUND

1. Field

The invention relates to processing of performance intensity zones.

2. Description of the Related Art

Use of performance intensity zones in sports is well-known. Polar Electro uses so-called sport zones: training is divided into a specific number of sport zones based on percentages of maximum heart rate. With sport zones, it is easy to select and monitor training intensities within a specific sport and follow sport zones-based training programs for that specific sport.

SUMMARY

According to an aspect of the present invention, there is provided an apparatus comprising: one or more processors, and one or more memories storing instructions, that, when executed by the one or more processors, cause the apparatus to: obtain performance intensity data measured from a user with at least one measurement sensor during a first activity and/or a second activity; and classify the performance intensity data in relation to a plurality of predetermined performance intensity zones, wherein each performance intensity zone is predetermined by a first numerical range for the first activity, and a second numerical range for the second activity, wherein the first activity and the second activity are at least one of different types of sports, different types of physical activities.

BRIEF DESCRIPTION OF DRAWINGS

Example embodiments of the present invention are described below, by way of example only, with reference to the accompanying drawings, in which.

DETAILED DESCRIPTION

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while FIGS. 1, 2, 3, 5, and 6 illustrate various embodiment of apparatuses, they are simplified block diagrams that only show some structures and functional entities. The connections shown in these Figures are logical connections; the actual physical connections may be different. Interfaces between the various elements may be implemented with suitable interface technologies, such as a message interface, a method interface, a sub-routine call interface, a block interface, or any hardware/software means enabling communication between functional sub-units. It is apparent to a person skilled in the art that the described apparatuses may also comprise other functions and structures. It should be appreciated that details of some functions, structures, and the protocols used for communication are irrelevant to the actual invention. Therefore, they need not be discussed in more detail here. Although the apparatuses have been depicted as separate single entities, different parts may be implemented in one or more physical or logical entities.

Figure 1:
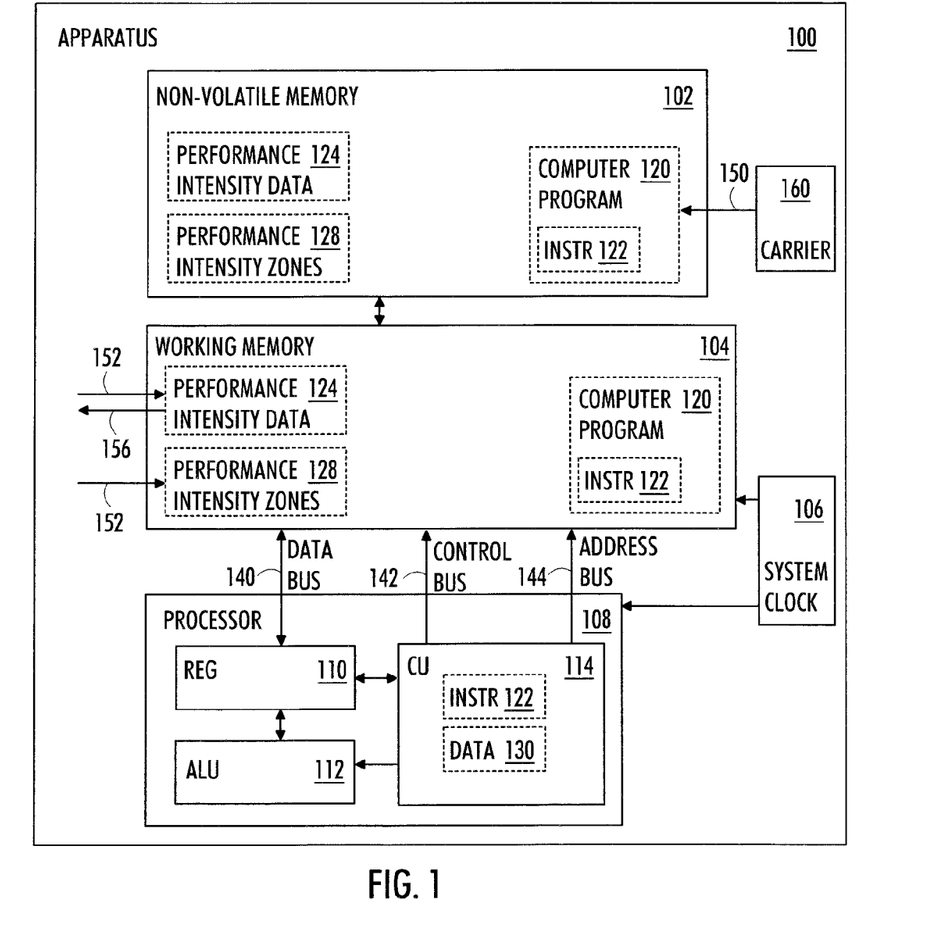
FIGS. 1, 2 and 3 illustrate example embodiments of various apparatuses.

As shown in FIG. 1, an apparatus 100 comprises one or more processors 108, and one or more memories 104, 102 storing instructions 122. The instructions 122, when executed by the one or processors 108, cause the apparatus 100 to obtain performance intensity data 124 measured from a user with at least one measurement sensor during a first activity and/or a second activity, and to classify the performance intensity data 124 in relation to a plurality of predetermined performance intensity zones 128. Each performance intensity zone 128 is predetermined by a first numerical range for the first activity, and a second numerical range for the second activity. Performance intensity data 124 characterizes the intensity of the physical activity, i.e. the rate at which human system works. The intensity of the physical activity has an effect on what fuel (fat, carbohydrates, proteins) the body uses and what kind of adaptations the body makes after the activity (=the training effect). In sport, the intensity of the physical activity is also known as the exercise intensity. The classification of the performance intensity data 124 means that a continuous data 124 measured during the activity is transformed into classified performance intensity data 124. The classified performance intensity data 124 may be summary data, for example, which indicates the amount of intensity for the user at each performance intensity zone 128 during the activity. The summary data may be expressed as amount of time spent at each performance intensity zone 128, for example.

Although two activities are defined, the first activity and the second activity, the example embodiments are not limited to such a configuration, but may be applied to even more than two activities. Consequently, an additional numerical range may be defined for each additional activity.

It is believed that the mechanism of exercise on human system is based on adaptation mechanism, where the human system aims to adapt to the requirements simulated with the exercise. The adaptation is believed to take place, when the human body is recovering after the exercise. The adaptation means that the person's performance improves in that specific exercise type.

Different performance intensities result in different adaptation in the human system. For example, low intensity performance improves fat burning, while high intensity exercise increases maximum performance In an example embodiment, performance intensity zones 128 may be defined as heart rate zones. Each heart rate zone is defined by a lower and upper limit, and the zones form a continuum between the lowest heart rate, such as rest heart rate, and the maximum heart rate. The heart rate limits defining the performance intensity zones 128 may be predefined or they may be calculated from heart rate variability in the beginning of the exercise, for example. A modern heart rate monitoring system, such as a wrist unit, a mobile phone with suitable software or a pre-analysis software in a PC or web service, is capable of showing the actual heart rate and the performance intensity zone 128 at which the heart rate is. When the performance intensity data 124 is classified in relation to a plurality of predetermined performance intensity zones 128, time that is accumulated at each performance intensity zone 128 may be calculated. The classified performance intensity data 124 may be compared with target values. The target values provide the recommendations in order to achieve a desired adaptation with the exercise.

Modern heart rate monitoring systems are designed to monitor multi-sport activities, such as those including running, swimming, cycling and many other sports, but they may also be used to monitor any physical activity. The different types of sports, or, different kinds of physical activities, exert the human body differently, and the human adaptation mechanism varies between different sports, or physical activities. The use of uniform performance intensity zones 128 for all types of sports or physical activities would result in inaccuracy of adaptation and erroneous performance instructions. In contrast, determining performance intensity zones 128 with own specific numerical ranges for each activity results in correct performance instructions as the adaptation is correctly defined for the individual person in each activity.

Figure 7:
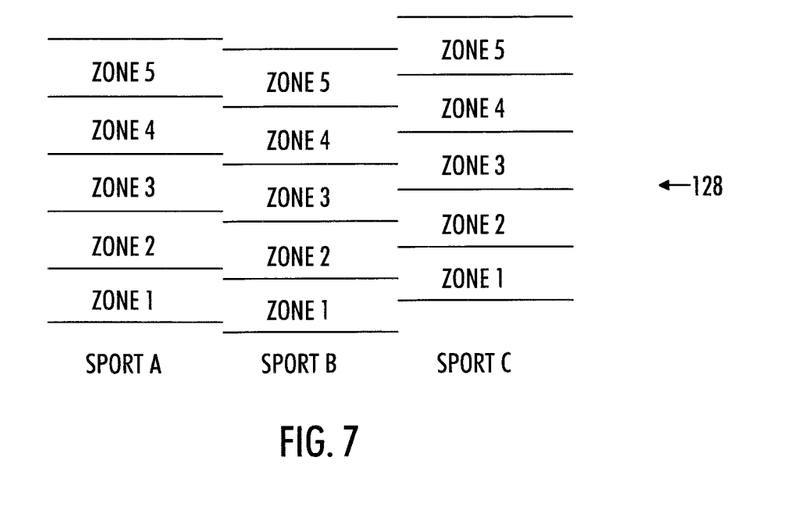
FIGS. 7 and 8 illustrate example embodiments of performance intensity zones.

An example embodiment of activity-specific performance intensity zones 128 is illustrated in FIG. 7: the entire performance scale is divided into five performance intensity zones 128: ZONE 1, ZONE 2, ZONE 3, ZONE 4, and ZONE 5. Naturally, the number of performance intensity zones 128 may vary according to the application. Each performance intensity zone 128 represents exertion limits corresponding to desired physiological adaptation. As shown in FIG. 7, there are specific numerical ranges for each activity: performance intensity zones of SPORT A are differently aligned from both performance intensity zones of SPORT B and from performance intensity zones of SPORT C.

Table 1 gives examples of performance intensity zones 128 and zone limits (speed/pace) for three different activities: running, cycling, and cross-country skiing.

TABLE 1

Performance intensity zones for three different activities

| Performance intensity zone | Meaning of performance intensity zone | Running (pace min/km) | Cycling (speed km/h) | Cross-country skiing (speed km/h) |
|---|---|---|---|---|
| 6 | Maximum | 3:00-4:00 | 40-50 | 15-20 |
| 5 | Very High | 4:00-4:30 | 35-40 | 13-15 |
| 4 | High | 4:30-5:00 | 30-35 | 10-13 |
| 3 | Moderate | 5:00-6:00 | 25-30 | 8-10 |
| 2 | Easy | 6:00-7:00 | 20-25 | 5-8 |
| 1 | Recovery | 7:00- | 0-20 | 0-5 |

In an example embodiment, the performance intensity zones 128 may be used for exercise planning. Heart rate monitoring systems have programmable training guidance features, which are based on performance intensity zones 128. The user inputs the desired training effect, such as weight loss, fitness improvement or maximum performance capability improvement, and the wrist unit, web service or PC software forms target times, which shall be accumulated at each performance intensity zone 128 in order to gain the desired training effect. The target time may be any measure, which accumulates and measures the amount of exercise. One measure may be energy expenditure. Another measure is the exercise time.

In an example embodiment, the performance intensity zones 128 may also be used for monitoring the exercise. The performance intensity data 124 (such as heart rate data, speed data, power data, and energy expenditure data) is classified, and the time or energy expenditure is summed up at every performance intensity zone 128. The accumulated values of the performance intensity data 124 at each performance intensity zone 128 indicate the training effect of the exercise or exercise. The classified accumulated values 124 may be compared with the target values and shown to the user.

In an example embodiment, the performance intensity data 124 and performance intensity zones 128 may be represented with different units, such as heart rate units (frequency unit (beats per minute) or time interval units (milliseconds)), speed units (min/km or km/h), power units (W), energy expenditure units (kcal/min), or training load units, for example.

In an example embodiment, the first numerical range may be represented with a first unit of measure, and the second numerical range may be represented with a second unit of measure, where the first unit of measure is different from the second units of measure. Such a scenario is illustrated in Table 1, wherein the first unit of measure for the first activity (running) is the pace (minutes/kilometer), and the second unit of measure for the second activity (cycling) is the speed (kilometers/hour). For this embodiment, the one or more memories 104 may further store instructions 122, that, when executed by the one or more processors 108, cause the apparatus 100 to output the performance intensity data 124 in an arbitrary unit of measure, which is different from the first unit of measure and the second unit of measure. The arbitrary unit may be a relative unit of measurement to show the ratio of amount of intensity to a predetermined reference measurement. The reference measurement may be defined by the manufacturer of the apparatus 100 based on experimentation or analysis of data collected from a number of subjects.

In another example embodiment, the first numerical range and the second numerical range are represented with a same specific unit of measure, and the first numerical range is different from the second numerical range. Such a scenario is illustrated in Table 2, wherein the specific unit of measure is the heart rate values for all activities (running, cycling, swimming, tennis). For this embodiment, the one or more memories 104 may further store instructions 122, that, when executed by the one or more processors 108, cause the apparatus 100 to output intensity data with the same specific unit of measure for the first activity and the second activity.

Table 2 illustrates a further example embodiment, where the first numerical range and the second numerical range may be presented by heart rate values.

In an example embodiment, the training intensity of each activity may be scaled so that all activities may be characterized with a single performance intensity zone 128 configuration. The scaling of the performance intensity zone 128 limits may be performed in various ways. Scaling may be performed by setting the maximum heart rate. The maximum heart rate is the largest value the person can achieve. The maximum heart rate is activity-specific: activities which apply large muscle groups result typically in larger maximum heart rate than activities where small muscle groups are applied. Also, the physical environment affects the maximum heart rate. Therefore, swimming is associated with lower maximum heart rate than running, for example. Table 2 illustrates an example of scaling the heart rate limits for various activities: running, cycling, swimming, and tennis. Note that lower limit values of each performance intensity zone 128 are shown in Table 2.

With reference to Table 2, let us study an example embodiment relating to the classification of performance intensity data 124. The user goes running and his target is to increase running speed. He runs for thirty minutes and the accumulated hear rate data is classified as follows: 5 minutes warm-up with the heart rate at performance intensity zones 2 and 3, i.e. the heart rate varies from 120 to 159 beats per minute, and 25 minutes speed-training with the heart rate at the performance intensity zone 4, i.e. the heart rate varies from 160 to 171 beats per minute. Such training develops his ability for speed. In the following day, he needs to have an exercise aiding recovery. He decides to go swimming, and, as can be seen from Table 2, the heart rate needs to vary from 100 to 116 beats per minute in order to remain in recovery performance intensity zone 128 determined for swimming.

TABLE 2

Performance intensity zones with heart rate values

| Performance intensity zone | Meaning of performance intensity zone | Running | Cycling | Swimming | Tennis |
|---|---|---|---|---|---|
|  | HRmax | 200 | 191 | 188 | 195 |
| 6 | Maximum | 180 | 175 | 172 | 178 |
| 5 | Speed II | 172 | 168 | 163 | 170 |
| 4 | Speed I | 160 | 156 | 150 | 155 |
| 3 | Basic II | 140 | 135 | 130 | 136 |
| 2 | Basic I | 120 | 117 | 111 | 117 |
| 1 | Recovery | 100 | 100 | 95 | 90 |

In an example embodiment, the one or more memories 104 may further store instructions 122, that, when executed by the one or more processors 108, cause the apparatus 100 to obtain a first maximum heart rate in the first activity and a second maximum heart rate in the second activity, and predetermine the performance intensity zone 128 by the first numerical range for the first activity as a first predetermined relation to the first maximum heart rate, and by the second numerical range for the second activity as a second predetermined relation to the second maximum heart rate. In such a scenario, the first activity and the second activity are handled independently. The maximum heart rate for each activity may be determined by a maximum heart rate test performed during each activity, for example.

The rest heart rate may also be taken into account. In such a modified example embodiment, the one or more memories 104 may further store instructions 122, that, when executed by the one or more processors 108, cause the apparatus 100 to perform at least the following: obtain a first maximum heart rate in the first activity, a second maximum heart rate in the second activity, and a rest heart rate, and predetermine the performance intensity zone 128 by the first numerical range for the first activity as a first predetermined relation to the first maximum heart rate and the rest heart rate, and by the second numerical range for the second activity as a second predetermined relation to the second maximum heart rate and the rest heart rate.

In another example embodiment, the one or more memories 104 may further store instructions 122, that, when executed by the one or more processors 108, cause the apparatus 100 to obtain a first maximum heart rate in the first activity, and predetermine the performance intensity zone 128 by the first numerical range for the first activity as a first predetermined relation to the first maximum heart rate, and by the second numerical range for the second activity as a second predetermined relation to the first maximum heart rate. In such a scenario, the first activity and the second activity are handled depending on each other. The maximum heart rate test needs only be performed for the first activity, for example.

If the rest heart rate is also taken into account, the example embodiment becomes as follows. The one or more memories 104 may further store instructions 122, that, when executed by the one or more processors 108, cause the apparatus 100 to obtain a first maximum heart rate in the first activity, and a rest heart rate, and predetermine the performance intensity zone 128 by the first numerical range for the first activity as a first predetermined relation to the first maximum heart rate and the rest heart rate, and by the second numerical range for the second activity as a second predetermined relation to the first maximum heart rate and the rest heart rate.

The performance intensity zones 128 may be adjusted according to the activity-specific maximum heart rate. The highest zone limit is typically adjusted according to the maximum heart rate, and the lowest limit may be fixed to the rest heart rate. In an embodiment, the user inputs maximum heart rates to the system, and the system calculates the zones. In another embodiment, the system examines the person's training files and tracks down the maximum heart rate values. It is also possible that the person inputs the maximum heart rate in one activity, such as running, and maximum heart rates are scaled according to general knowledge of the heart rate maxima in different activities.

In an example embodiment, the performance intensity zones 128 may also be defined according to person's current adaptation level to the activities under consideration. It is possible that the person's adaptation varies from one activity to another. If person has actively been exercising running, for example, and starts practicing triathlon (including, besides running, also swimming and cycling), it is very likely that the performance intensity zones 128 are different for each activity. Performance intensity zones 128 for running are higher than those of cycling and swimming The user may input the amount in weekly hours of each activity into the system. The system may assess the adaptation level and adjust the performance intensity zones 128 accordingly taking into account the targets set by the user. In one embodiment, the system monitors the training history and adjusts the performance intensity zones 128 according to assumed adaptation.

In an example embodiment, the memory 104 may further store instructions 122, that, when executed by the processor 108, cause the apparatus 100 to obtain first training time of the first activity and a second training time of the second activity from an analysis of the performance intensity data 124, and adjust the first numerical range and/or the second numerical range on the basis of the first training time and/or the second training time.

Tables 1 and 2 show the performance intensity zones 128 in the same units. In one embodiment, the performance intensity zone limits are indicated with different units. For example, generic sports, such as a ballgame, may be characterized with heart rate units (beats per minute), while another sport such as cycling may be characterized with pedaling power. One further sport, such as running, may be characterized with running speed. Each activity, however, is divided into same number of performance intensity zones 128, where each performance intensity zone represents a specific adaptation type.

Figure 8:
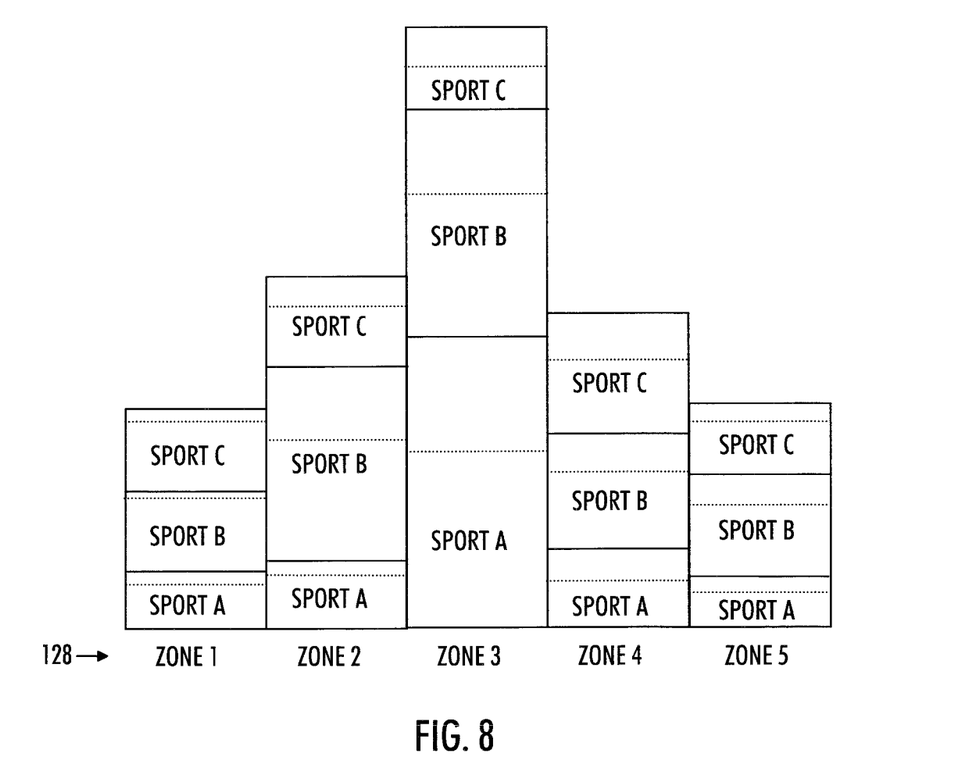

FIG. 8 illustrates an example embodiment of displaying the sport-specific performance intensity zone 128 information to the user. Each performance intensity zone ZONE 1-ZONE 5 consists of a histogram whose height represents the target accumulation (time or energy expenditure). Each performance intensity zone 128 comprises sub-histograms, where each sub-histogram represents the target accumulation in a specific activity SPORT A, SPORT B, SPORT C. The solid lines represent the target while the dotted lines show the actual accumulation at each sub-histogram.

With the above-described processing, the predetermined performance intensity zones 128 become activity-specific. As illustrated in Tables 1 and 2, and in FIG. 7, the scale (with zones 1 to 5 or with zones 1 to 6) is specified for each activity in such a manner that each zone is determined by the activity-specific numerical range for each activity. In effect, the (activity-specific) performance intensity zone 128 is specified by a numerical range of performance intensity specific for just that activity.

In an example embodiment, the performance intensity zones 128 are a plurality of numerical ranges of performance intensity in running, thus resulting in a plurality of running-specific performance zones.

In an example embodiment, the running-specific performance intensity zones 128 are specified by heart rate ranges.

In an example embodiment, the running-specific performance intensity zones 128 are specified by estimated energy expenditure rate ranges. An energy expenditure rate characterizes the rate at which a human system burns energy reserves.

In an example embodiment, the running-specific performance intensity zones 128 are specified by gait performance parameter ranges. Such gait performance parameters include running speed, running cadence, stance time (contact time) and swing time.

In an example embodiment, the performance intensity zones 128 are a plurality of numerical ranges of performance intensity in swimming, thus resulting in a plurality of swimming-specific performance intensity zones 128.

In an example embodiment, the swimming-specific performance intensity zones 128 are specified by heart rate ranges.

In an example embodiment, the swimming-specific performance intensity zones 128 are specified by stroke frequency ranges.

In an example embodiment, the swimming-specific performance intensity zones 128 are specified by swimming speed ranges.

In an example embodiment, the performance intensity zones 128 are a plurality of numerical ranges of performance intensity in cycling, thus resulting in a plurality of cycling-specific performance intensity zones 128.

In an example embodiment, the cycling-specific performance intensity zones 128 are specified by heart rate ranges.

In an example embodiment, the cycling-specific performance intensity zones 128 are specified by pedalling cadence ranges.

In an example embodiment, the cycling-specific performance intensity zones 128 are specified by cycling speed ranges.

In an example embodiment, the cycling-specific performance intensity zones 128 are specified by pedalling power ranges.

In an example embodiment, the performance intensity zones 128 are a plurality of numerical ranges of performance intensity in generic sports, thus resulting in a plurality of generic sports-specific performance zones 128. A generic sport includes a group of sports which excluded other sports defined by sport-specific performance intensity zones.

In an example embodiment, the generic sports-specific performance intensity zones 128 are specified by heart rate ranges.

In an example embodiment, the generic sports-specific performance intensity zones 128 are specified by motion intensity ranges. Motion intensity may be represented with motion pulse rate, acceleration measures, velocity measures, force measures, and/or energy expenditure rate measures measured with an accelerometer, for example.

Let us now return back to FIG. 1 in order to study an example embodiment of the apparatus 100 further. The term 'processor' 108 refers to a device that is capable of processing data. Depending on the processing power needed, the apparatus 100 may comprise several processors 108 such as parallel processors. When designing the implementation of the processor 108, a person skilled in the art will consider the requirements set for the size and power consumption of the apparatus 100, the necessary processing capacity, production costs, and production volumes, for example. The processor 108 and the memory 104, 102 may be implemented by an electronic circuitry. In an example embodiment, the processor 108 is Epson S1C88650 (8-bit) and the memory 104, 102 is EEPROM 128 kB, EEPROM 1 MB, EEPROM 2×512 kB, EEPROM 2×1 MB, or Flash 4 MB, for example.

A non-exhaustive list of implementation techniques for the processor 108 and the memory 104, 102 includes, but is not limited to:
 logic components,
 standard integrated circuits,
 application-specific integrated circuits (ASIC),
 system-on-a-chip (SoC),
 application-specific standard products (ASSP),
 microprocessors,
 digital signal processors,
 special-purpose computer chips, and
 field-programmable gate arrays (FPGA).

The instructions 122 may be implemented by software and/or hardware. In an example embodiment, the software may be written by a suitable programming language (such as C, C++, or Java), and the resulting executable instructions 122 may be stored on the memory 104 and run by the microprocessor 108. In an example embodiment, the functionality of the hardware may be designed by a suitable hardware description language (such as Verilog or VHDL), and transformed into a gate-level netlist (describing standard cells and the electrical connections between them), and after further phases the chip implementing the processor 108, memory 104 and the instructions 122 may be fabricated with photomasks describing the circuitry.

In an example embodiment, the apparatus 100 may be a wrist-worn sports computer, a bicycle computer, a mobile phone, a tablet pc, a portable computer, a computer, a server computer, a server computer accessible over a data network, or any other suitable apparatus for processing the performance intensity data 124, or a suitable portable apparatus. Such example embodiments will be explained with reference to FIGS. 2, 3, 5 and 6.

However, in an example embodiment, the apparatus 100 may also be interpreted as a circuitry implementing the required functionality within some suitable equipment.

If the apparatus 100 is an independent apparatus, then it may also comprise equipment needed for other tasks as well. On the other hand, if the apparatus 100 is the circuitry, then it may only comprise the processor 108, the memory 104, the instructions 122, and interfaces enabling communication with other devices, an interface 152 for inputting the performance intensity data 124, an interface 154 for inputting the performance intensity zones 128, and an interface 156 for outputting the (classified) performance intensity data 124, for example.

In an example embodiment, the apparatus 100 may be an electronic digital computer, which may comprise, besides the processor 108 and the (working and/or non-volatile) memory 104, 102 a system clock 106, as illustrated in FIG. 1. Furthermore, the computer may comprise a number of peripheral devices. Naturally, the computer may comprise a number of other peripheral devices, not illustrated here for the sake of clarity.

In an example embodiment, the system clock 106 constantly generates a stream of electrical pulses, which cause the various transferring operations within the computer to take place in an orderly manner and with specific timing.

In an example embodiment, the processor 108 may be implemented as a microprocessor implementing functions of a central processing unit (CPU) on an integrated circuit. The CPU 108 is a logic machine executing a computer program 120, which comprises the program instructions 122. The instructions 122 may be coded as a computer program using a programming language, which may be a high-level programming language, such as C, or Java, or a low-level programming language, such as a machine language, or an assembler. The CPU 108 may comprise a set of registers 110, an arithmetic logic unit (ALU) 112, and a control unit (CU) 114. The control unit 114 is controlled by a sequence of instructions 122 transferred to the CPU 108 from the working memory 104. The control unit 114 may contain a number of microinstructions for basic operations. The implementation of the microinstructions may vary, depending on the CPU 108 design. The microprocessor 108 may also have an operating system (a dedicated operating system of an embedded system, or a real-time operating system), which may provide the computer program 120 with system services.

In an example embodiment, there may be three different types of buses between the working memory 104 and the processor 108: a data bus 140, a control bus 142, and an address bus 144. The control unit 114 uses the control bus 142 to set the working memory 104 in two states, one for writing data into the working memory 104, and the other for reading data from the working memory 104. The control unit 114 uses the address bus 144 to send to the working memory 104 address signals for addressing specified portions of the memory in writing and reading states. The data bus 140 is used to transfer data 130, such as the performance intensity data 124 and performance intensity zones 128, from the working memory 104 to the processor 108 and from the processor 108 to the working memory 104, and to transfer the instructions 122 from the working memory 104 to the processor 108.

In an example embodiment, the working memory 104 may be implemented as a random-access memory (RAM), where the information is lost after the power is switched off. The RAM is capable of returning any piece of data in a constant time, regardless of its physical location and whether or not it is related to the previous piece of data. The data may comprise exercise data, user profiles, any temporary data needed during the processing, program instructions etc.

In an example embodiment, the non-volatile memory 102 retains the stored information even when not powered. Examples of non-volatile memory include read-only memory (ROM), flash memory, magnetic computer storage devices such as hard disk drives, and optical discs. As is shown in FIG. 1, the non-volatile memory 102 may store both data 124, 128 and the computer program 120 comprising the instructions 122.

An example embodiment provides a computer program 120 comprising the instructions 122 which, when loaded 150 into the apparatus 100, cause the apparatus 100 to obtain performance intensity data 124 measured from a user with at least one measurement sensor during a first activity and/or a second activity, and to classify the performance intensity data 124 in relation to a plurality of predetermined performance intensity zones 128, wherein each performance intensity zone 128 is predetermined by a first numerical range for the first activity, and a second numerical range for the second activity.

In an example embodiment, the computer program 120 may be in source code form, object code form, or in some intermediate form. The computer program 120 may be stored in a carrier 160, which may be any entity or device capable of carrying the program 120 to the apparatus 100. The carrier 160 may be a computer-readable storage medium. Besides this, the carrier 160 may be implemented as follows, for example: the computer program 120 may be embodied on a record medium, stored in a computer memory, embodied in a read-only memory, carried on an electrical carrier signal, carried on a telecommunications signal, and/or embodied on a software distribution medium. In some jurisdictions, depending on the legislation and the patent practice, the carrier 160 may not be the telecommunications signal. The medium 160 may be a non-transitory computer-readable storage medium.

FIG. 1 illustrates an example embodiment in which the carrier 160 may be coupled 150 with the apparatus 100, whereupon the program 120 comprising the instructions 122 is transferred into the working memory 104, and possibly also into the non-volatile memory 102. The program 120 with its instructions 122 may be loaded from the non-volatile memory 102 into the working memory 104 as needed. During running of the program 120, the instructions 122 are transferred via the data bus 140 from the working memory 104 into the control unit 114, wherein usually a portion of the instructions 122 resides and controls the operation of the apparatus 100.

There are many ways to structure the program 120. In an example embodiment, the operations of the program may be divided into functional modules, sub-routines, methods, classes, objects, applets, macros, etc., depending on the software design methodology and the programming language used. In modern programming environments, there are software libraries, i.e. compilations of ready-made functions, which may be utilized by the program for performing a wide variety of standard operations.

Figure 2:
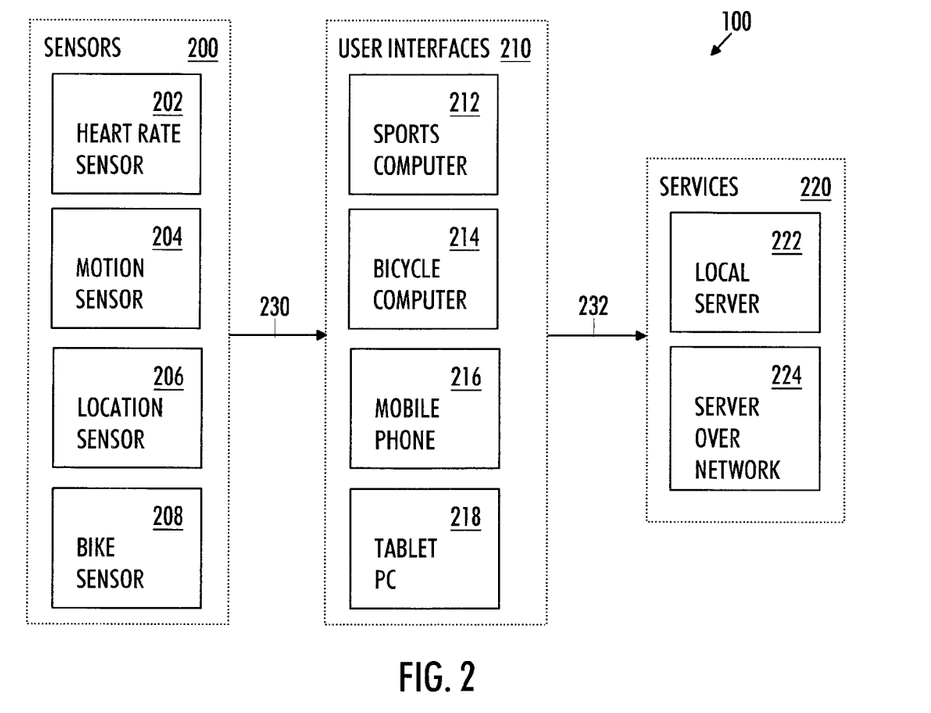

In an example embodiment, illustrated in FIG. 2, the apparatus 100 may be implemented within a training system comprising sensors 200, user interfaces 210 and services 220. The sensors 200 produce the performance intensity data 124. A non-exhaustive list of sensors 200 includes heart rate sensors 202, motion sensors 204, location sensors 206 and bike sensors 208, as well as other sensors utilized in training systems to gather information regarding the training. The heart rate sensors 202 include, but are not necessarily limited to, a cardiovascular sensor (such as an electrocardiogram ECG sensor), and an optical heart rate sensor (heart rate, heart rate variability). Motion sensors 204 may include accelerometers worn on chest, wrist, or ankle. Location sensors 206 may utilize GPS (Global Positioning System) or other satellite-based, or radio system-based system for locating the user and measuring various parameters (speed, distance, location, route) relating to the movement of the user. Bike sensors 208 may be sensors attached to various parts of the bike for measuring speed, cadence, or power, for example.

The user interfaces 210 may be implemented on any suitable electronic apparatus such as a sports computer 212 worn on wrist, a bicycle computer 214, a mobile phone 216, and a tablet PC 218 or other suitable computer. The user interface 210 apparatuses may perform the described classification of the performance intensity data 124, and/or perform the presentation of the performance intensity data 124 and possibly also the manipulation of the parameters relating to the described processing (adjustment of performance intensity zones 128, for example).

The services 220 may be implemented in local server 222 running a PC application, or in a server 224 accessible over a data network (such as the Internet), for example. The classification of the performance intensity data 124 may also be performed with the services 220.

In an example embodiment, algorithms or a part of the algorithms may be run in any part 200, 210, 220 of the system. User setting may be done in the service 220 and/or in the user interface 210. The information may be displayed in the service 220 and/or in the user interface 210. The sensors 200 may be coupled 230 with the user interfaces 210. The user interfaces 210 may be coupled 232 with the services 220.

Figure 3:
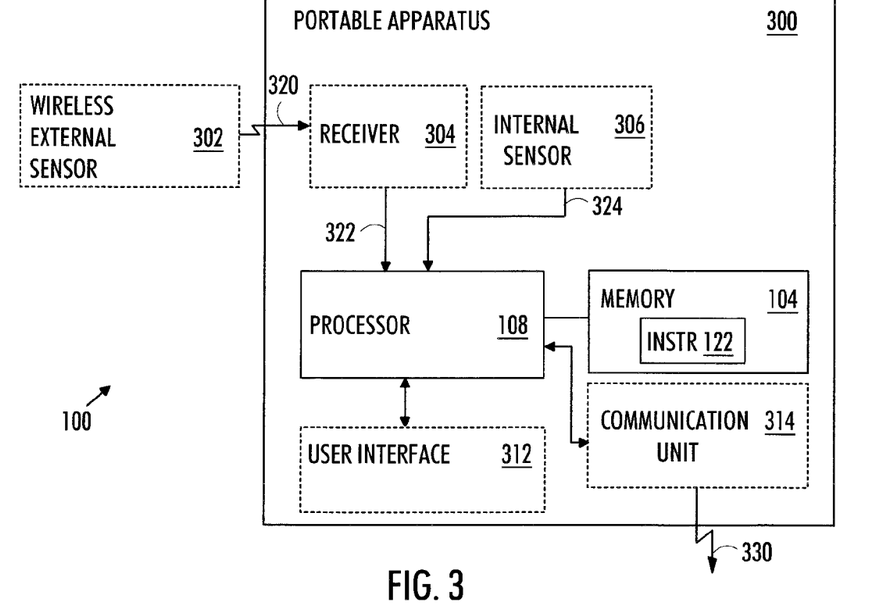

FIG. 3 illustrates example embodiments of a portable apparatus 300, capable of implementing at least some functionality of the apparatus 100, i.e. sensors 200, user interfaces 210, and/or services 220. The portable apparatus 300 comprises the processor 108, the memory 104, and the instructions 122. The processor 108 is configured to obtain performance intensity data 124 measured from a user with at least one measurement sensor during a first activity and/or a second activity; and to classify the performance intensity data 124 in relation to a plurality of predetermined performance intensity zones 128, wherein each performance intensity zone 128 is predetermined by a first numerical range for the first activity, and a second numerical range for the second activity.

The user interface part 312 of the portable apparatus 300 may be worn around the wrist, like a watch, but it may well be implemented in another kind of platform, such as a subscriber terminal of a radio system: a mobile telephone for example. The user interface part may also be a sports watch for use as an instrument in sports. Polar Electro® (www.polarelectro.com) designs and manufactures such apparatuses 100 and their accessories. At the time of filing this patent application, the portable apparatus 300 may be implemented based on a Polar sports computer RCX5, for example. The implementation of the embodiments in such an existing product requires relatively small and well-defined modifications. Naturally, as the products evolve, feasible platforms for the implementation of the embodiments described in this patent application also evolve and emerge.

In an example embodiment, the portable apparatus 300 may be a heart rate monitor for measuring the performance intensity data 124 such as user's heart rate and possibly other physiological parameters that can be measured from the user. In U.S. Pat. No. 4,625,733, which is incorporated herein by reference, Saynajakangas describes a wireless heart rate monitoring concept where a transmitter attached to the user's chest measures the user's heart rate and transmits heart rate information telemetrically to a heart rate receiver attached to the user's wrist. The transmission of the heart activity data may utilize the principles of time division and/or packet transmission, for example.

Other implementations may also be possible. The heart rate monitor may also be implemented such that the heart rate is directly measured from the wrist on the basis of pressure or optical measurement, for example. Other ways for measuring the heart rate may also be employed. As sensor technology becomes more integrated, less expensive, and its power consumption characteristics are improved, a sensor measuring heart activity data may also be placed in arrangements other than the chest strap transmitter. Polar Electro is already marketing apparels which comprise integrated electrode structures.

Figure 6:
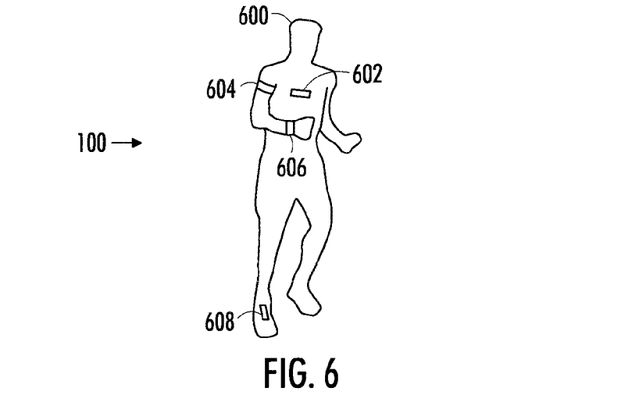
FIG. 6 illustrates an example embodiment of a wrist-worn sports computer.

FIG. 6 illustrates an example embodiment where the apparatus 100 is implemented as a running computer, such as Polar RCX5. A runner 600 is provided with the following equipment: a wrist receiver 606, a heart rate transmitter 602, an upper-arm-mounted positioning receiver 604, and a shoe-mounted stride sensor 608. The accessories 602, 604, 608 communicate wirelessly with the wrist receiver 606. Various accessories may be flexibly used as needed, i.e. all of them are not necessarily needed all the time, or by all users, or in all use cases.

The positioning receiver 604 receives external location information, which may be utilized to generate the performance intensity data 124. The positioning receiver 604 may be a receiver of a global navigation satellite system. Such a system may be the Global Positioning System (GPS), the Global Navigation Satellite System (GLONASS), the Galileo Positioning System (Galileo), the Beidou Navigation System, or the Indian Regional Navigational Satellite System (IRNSS), for example. The positioning receiver 604 determines its location (longitude, latitude, and altitude) using signals transmitted from satellites orbiting the earth. Besides global navigation satellites, the positioning receiver 604 may also determine its location by utilizing other known positioning techniques. It is well known that by receiving radio signals from several different base stations, a mobile phone may determine its location, for example.

In summary, the portable apparatus 300 may be such that it comprises at least one measurement sensor 302, 306, which measures some aspect of the physical activity (such as exercise) in order to obtain the performance intensity data 124. The measurement sensor may be an internal measurement sensor 306, which is physically coupled (by a wiring on a printed circuit board, for example) with the portable apparatus 300. The measurement sensor may also be a wireless external sensor 302. The wireless external sensor 302 may be coupled by electric and/or magnetic radiation 320 with a receiver (implemented by an integrated circuit, for example) 304 of the portable apparatus 102. The measurement sensor 302, 306 may provide 322, 324 the performance intensity data 124 as raw measurement data without further processing to the processor 108, or the measurement sensor 302, 306 may process the raw data before providing 322, 324 it as the performance intensity data 124 to the processor 108.

In an example embodiment, the portable apparatus 300 may comprise a user interface 312. The user interface 312 may comprise a display, means for producing sound, a keyboard, and/or a keypad, for example. The display may be a liquid crystal display, for example, but it may also be implemented by any appropriate prior art technique, such as with an active-matrix organic light-emitting diode. The display may also incorporate other user interaction means, such as touch input, or haptic feedback, i.e. the display may be a touch screen. The means for producing sound may be a loudspeaker or a simpler means for producing beeps or other sound signals. The keyboard/keypad may comprise a complete (qwerty) keyboard, a mere numeric keypad or only a few push buttons and/or rotary buttons. In addition, the user interface 312 may comprise other prior art user interface elements, for example various means for focusing a cursor (mouse, track ball, various arrow keys, touch sensitive area etc.) or elements enabling audio control. A parameter relating to the exercise (such as the performance intensity data 124 before and/or after the classifications) or a setting (such as the performance intensity zones 128 and their numerical ranges for each activity) of the portable apparatus 300 may be shown on the user interface 312, on the display, for example.

In an example embodiment, the portable apparatus 300 may comprise an output device configured to output 330 a parameter such as the classified performance intensity data 124. The output device may be, for example, a part of the user interface 312 of the portable apparatus 300: the parameter may be outputted on a display of the portable apparatus 300, for example. The output device may also be an interface via which the parameter may be transferred to another device. Such an interface may be wired or wireless. Examples of such technologies include a communication bus, such as Universal Serial Bus USB, or some other serial/parallel bus, or a radio transceiver 314 (such as Bluetooth or some other standard or proprietary communication protocol).

FIG. 3 further describes an example embodiment, wherein the apparatus 100/300 comprises at least one input interface 320, 322, 324 for the at least one measurement sensor 302, 306. As was explained earlier, the at least one measurement sensor 302, 306 may comprise at least one of the following: a heart rate sensor 202, a motion sensor 204, a location sensor 206, a bike sensor 208.

In another example embodiment, the apparatus 100/300 may further comprise a first input interface 320, 322 for a first measurement sensor 302 for measuring the first activity, and a second input interface 324 for a second measurement sensor 306 for measuring the second activity. In this example embodiment, the first measurement sensor 302 and the second measurement sensor 306 are selected from a heart rate sensor 202, a motion sensor 204, a location sensor 206, and a bike sensor 208 such that the first measurement sensor 302 is not of the same type as the second measurement sensor 306.

In an example embodiment, the second (internal) measurement sensor 306 is the motion sensor 204, and the first (wireless external) measurement sensor 302 is the heart rate sensor 202, the location sensor 206, or the bike sensor 208.

In an example embodiment, the apparatus 100/300 may also be based on an existing activity monitor such as Polar Electro's FA20 Activity Computer. The measurement sensor 302, 306 may be an accelerometer for producing the performance intensity data 124. The accelerometer measures its own motion, acceleration, i.e. the rate of change in velocity, and converts the acceleration into an electric signal. The electric signal is converted into a digital format in an AD converter. Acceleration may be expressed by the unit of measurement g. One g is the acceleration caused to an object by earth's gravity. Accelerations between −2 and +2 g may usually be measured from human movement.

The accelerometer may be placed, during use, on the chest, in the wrist, on foot, at waist level, or in pocket, for example. From the acceleration, various parameters may be calculated, such as the speed, energy consumption, or motion frequency (such as the number of steps in walking or running, pedalling cadence in bicycling, or the number of strokes in swimming).

Various techniques may be used for measuring acceleration. Piezo-resistor technology employs material whose resistance changes as it compresses. The acceleration of mass produces a force in a piezo-resistor. If a constant current is supplied through the piezo-resistor, its voltage changes according to the compression caused by acceleration. In piezo-electric technology, a piezo-electric sensor generates charging when the sensor is accelerated. In silicon bridge technology, a silicon chip is etched so that a silicon mass remains on it at the end of a silicon beam. If acceleration is directed to the silicon chip, the silicon mass focuses a force on the silicon beam, thus changing the resistance of the silicon beam. Micro-machined silicon technology is based on the use of a differential capacitor. Voice coil technology is based on the same principle as a microphone. Examples of suitable movement sensors include: Analog Devices ADXL105, Pewatron HW or VTI Technologies SCA series. The implementation of the accelerometer may also be based on other appropriate techniques, for example on a gyroscope integrated into a silicon chip or on a micro vibration switch incorporated into a surface mounting component.

Figure 5:
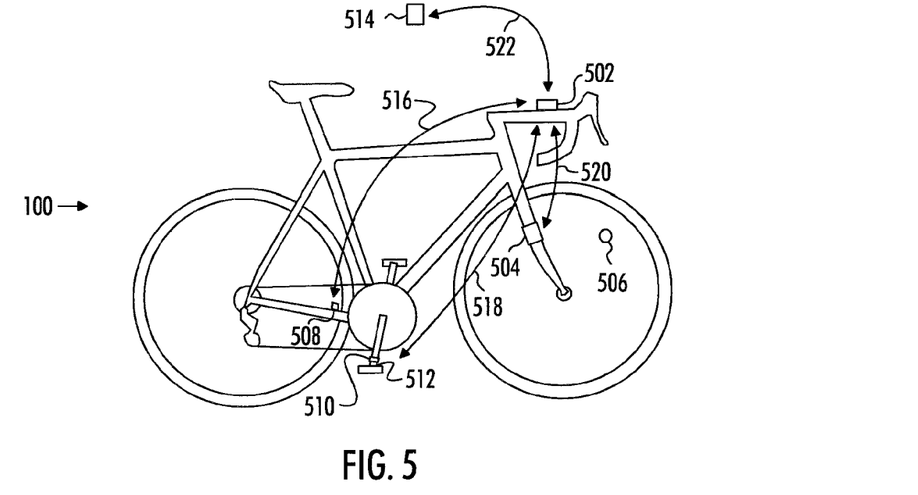
FIG. 5 illustrates an example embodiment of a bicycle computer.

FIG. 5 illustrates an example embodiment where at least a part of the apparatus 100 is implemented in a cycling computer system. Many of the parameters, described later on, produced by such cycling computer system may be utilized as the performance intensity data 124. At the time of filing this patent application, such a cycling computer system may be implemented based on a Polar CS500 with a power sensor, for example. The implementation of the embodiments in such an existing product requires relatively small and well-defined modifications. Naturally, as the products evolve, feasible platforms for the implementation of the embodiments described in this patent application also evolve and emerge.

In an example embodiment, the apparatus 100 may comprise a handlebar-mounted central unit 502. The central unit 502 may be a bike computer, a mobile phone, or a wrist computer, for example. The user interface run in the central unit 502 may show various cycling-related parameters, such as elapsed time, speed, distance, elevation, cadence, route information etc. At least the speed may be utilized as the performance intensity data 124. The user interface may be implemented in a similar fashion as was earlier described for the portable apparatus 300.

Furthermore, the central unit 502 may output information relating to the measured elastic strain in an example embodiment. A pedalling measurement unit 512 may measure elastic strain that may be transformed into pedalling action information, such as information on pedalling power, pedalling efficiency, left/right (crank) balance, and pedalling index. The outputted information may also relate to some other pedalling parameter, such as a scalar pedalling force, a tangential pedalling force, a radial pedalling force, a pedalling force distribution along pedalling angle, a maximum force, an average force etc. Such pedalling information may be utilized as the performance intensity data 124. The pedalling measurement unit 512 may transmit the measured elastic strain data, or further refined pedalling effort signal, using a wireless connection 518 to the central unit 502. The pedalling measurement unit 512 may comprise a wireless transmitter for transmitting the information to the central unit 502. The transmitter may operate according to a suitable proximity communication, i.e. with a communication technology that takes place over relatively small distances. A suitable range may vary from 0.5 to 1.5 meters. Longer ranges (such as ten meters) may also be applied. The range may be such that it encompasses typical communication path lengths within a bicycle. The proximity communication may be implemented with an induction-based technology utilizing a magnetic field, or a radio-based technology utilizing electric radiation, for example. It is to be noted that both technologies involve both the magnetic field and the electric radiation, but the separation is based on the fact that either one of these physical phenomena predominates and is used for communication in each technology. The induction-based transmission may operate at a kilohertz range frequency (5 kilohertz, 125 kilohertz, or over 200 kilohertz, for example). The radio transmission may utilize a proprietary transceiver (operating at a 2.4 gigahertz frequency, for example), or a Bluetooth transceiver, for example. Emerging ultra-low power Bluetooth technology may also be used. Other suitable proximity communication techniques may include techniques based on light or sound, such as infrared communication or sonic communication. The proximity communication may utilize any suitable protocols: the principles of time division and/or packet transmission, for example. The transmitter may be an induction-based transmitter, such as a kilohertz-range transmitter, a passive radio-frequency identification tag, a coil-based inductive communication unit, or a near field communication transmitter, for example. The radio transmission may also operate according to some WLAN (Wireless Local Area Network) standard.

Additionally, or alternatively, the pedalling measurement unit 512 may comprise a processor configured to form a pedalling parameter by using the elastic strain.

In an example embodiment, the apparatus 100 may also comprise a speed measuring unit 504, 506 for producing the performance intensity data 124. The speed measuring unit may comprise two parts, a speed detector 504, and a speed inductor 506. This may be implemented in such a manner that a wheel speed sensor 504 is placed on the fork, and a wheel speed magnet 506 is placed on a spoke (for the sake of clarity, spokes are not illustrated in FIG. 5). Speed information is obtained from the wheel speed sensor 504 as the wheel speed magnet 506 passes it. The speed detector 504 may transmit the wireless speed signal 520 to the central unit 502.

In an example embodiment, the apparatus 100 may also comprise a cadence measuring system 508, 510. The cadence may also be utilized in forming the performance intensity data 124. The cadence measuring system may comprise two parts, a cadence detector 508, and a cadence inductor 510. This may be implemented in such a manner that a cadence magnet 510 is placed on the crank, and the crank speed detector 508 is mounted on the chain stay. Cadence information is obtained from the crank speed detector 508 as the cadence magnet 510 passes it. The cadence detector 508 may transmit the wireless cadence signal 516 to the central unit 502. Alternatively, the cadence measuring system may be implemented with at least one accelerometer attached to the crank.

In an example embodiment, the apparatus 100 may also comprise a heart activity measurement unit 514. The heart activity measurement unit 514 may be strapped around the chest of the cyclist, for example. The heart activity measurement unit 514 may produce heart activity information, such as a heart rate, for the performance intensity data 124. The heart activity measurement unit 514 may transmit the wireless heart activity signal 522 to the central unit 502.

However, the example embodiments are not limited to the examples of FIGS. 3, 5 and 6, but the embodiments may be applied to any apparatus 100 used to process data relating to a physical exercise performed by the user of the apparatus 100. The term '(physical) activity refers to physical exercise, workout, sports, fitness exercise, and, in general, to any bodily activity of the user, even to normal activities (such as cleaning or any other housekeeping activities) during the everyday life. Some physical activities may enhance or maintain physical fitness and overall health and wellness.

Figure 4:
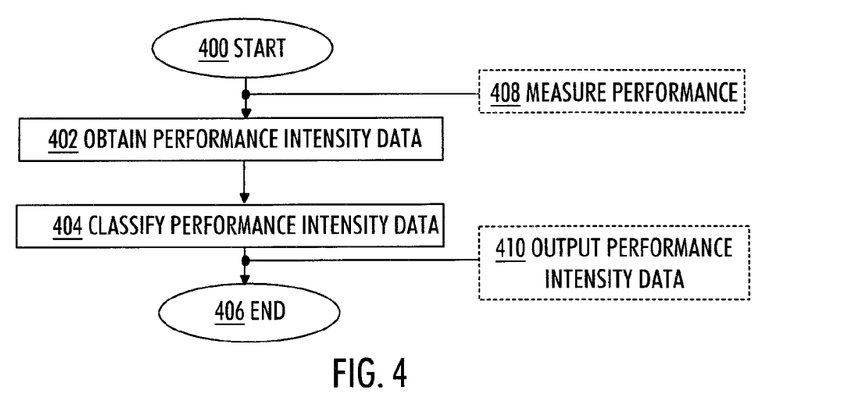
FIG. 4 illustrates example embodiments of a method.

Next, example embodiments of a method will be described with reference to FIG. 4. Other functions, not described in this application, may also be executed between the operations or within the operations. Some of the operations or parts of the operations may also be left out or replaced by a corresponding operation or part of the operation. The method starts in 400. In 402, performance intensity data measured from a user with at least one measurement sensor during a first activity and/or a second activity is obtained. In 404, the performance intensity data is classified in relation to a plurality of predetermined performance intensity zones, wherein each performance intensity zone is predetermined by a first numerical range for the first activity, and a second numerical range for the second activity. The method ends in 406.

In an example embodiment, the method may be performed either in real-time or after the actual exercise. In either case, the performance data is first measured in 408 before it is obtained in 402. In real-time case, the obtainment of the performance data and its classification in 402 and 404 is done during the exercise in real-time or almost in real-time. In the non-real-time case, there may be a time lag of minutes, hours, days, or even longer time periods between the actual measurement in 408, and the classification in 404.

In an example embodiment, the performance intensity data from the user is measured 408 with the at least one measurement sensor during the first activity and/or the second activity, the at least one measurement sensor comprising at least one of the following: a heart rate sensor 202, a motion 204 sensor, a location sensor 206, a bike sensor 208.

In another example embodiment, the first activity is measured 408 with a first measurement sensor and the second activity is measured 408 with the second measurement sensor, the first measurement sensor and the second measurement sensor being selected from a heart rate sensor 202, a motion sensor 204, a location sensor 206, and a bike sensor 208 such that the first measurement sensor is not of the same type as the second measurement sensor. In a further example embodiment, the second measurement sensor is the motion sensor 204, and the first measurement sensor is the heart rate sensor 202, the location sensor 206, or the bike sensor 208.

The embodiments of the earlier described apparatus 100 may also be used to enhance the method. In an example embodiment, the method may be implemented in an electronic apparatus 100 described earlier. In an embodiment, a computer program comprises instructions which, when loaded into an apparatus, cause the apparatus to perform the described process. In an embodiment, a computer-readable storage medium comprises the computer program.

Next, further example embodiments of the method will be described. These example embodiments may be freely combined with each other in order to produce further example embodiments.

In an example embodiment, the first numerical range and the second numerical range are represented with the same specific units of measure, and the first numerical range is different from the second numerical range, and the method further comprises: outputting 410 the performance intensity data with the same specific units of measure for the first activity and the second activity.

In an example embodiment, the first numerical range is represented with first units of measure, the second numerical range is represented with second units of measure, and the first units of measure are different from the second units of measure, and the method further comprises: outputting 410 the performance intensity data in arbitrary units of measure, which are different from the first units of measure and the second units of measure.

In an example embodiment, the first numerical range and the second numerical range are presented by heart rate values, and the method comprises at least one of the following:
obtaining a first maximum heart rate in the first activity and a second maximum heart rate in the second activity, and predetermine the performance intensity zone by the first numerical range for the first activity as a first predetermined relation to the first maximum heart rate, and by the second numerical range for the second activity as a second predetermined relation to the second maximum heart rate;

obtaining a first maximum heart rate in the first activity, and predetermine the performance intensity zone by the first numerical range for the first activity as a first predetermined relation to the first maximum heart rate, and by the second numerical range for the second activity as a second predetermined relation to the first maximum heart rate;

obtaining a first maximum heart rate in the first activity, a second maximum heart rate in the second activity, and a rest heart rate, and predetermine the performance intensity zone by the first numerical range for the first activity as a first predetermined relation to the first maximum heart rate and the rest heart rate, and by the second numerical range for the second activity as a second predetermined relation to the second maximum heart rate and the rest heart rate;

obtaining a first maximum heart rate in the first activity, and a rest heart rate, and predetermine the performance intensity zone by the first numerical range for the first activity as a first predetermined relation to the first maximum heart rate and the rest heart rate, and by the second numerical range for the second activity as a second predetermined relation to the first maximum heart rate and the rest heart rate;

obtaining first training time of the first activity and a second training time of the second activity from an analysis of the performance data, and adjust the first numerical range and/or the second numerical range on the basis of the first training time and/or the second training time.

The present invention is applicable to apparatuses 100 defined above but also to other suitable training systems. The protocols used, the specifications of training systems, and the apparatuses develop rapidly. Such development may require extra changes to the described example embodiments. Therefore, all words and expressions should be interpreted broadly and they are intended to illustrate, not to restrict, the example embodiments. It will be obvious to a person skilled in the art that, as technology advances, the inventive concept can be implemented in various ways. The invention and its embodiments are not limited to the examples described above but may vary within the scope of the claims.

The invention claimed is:

1. An apparatus comprising:
    one or more processors;
    one or more measurement sensors operatively coupled to the one or more processors; and
    one or more memories storing instructions that, when executed by the one or more processors, cause the apparatus to perform operations comprising:
    obtaining performance intensity data measured from a user, using the one or more measurement sensors, during at least one of a first activity and a second activity; and
    classifying the performance intensity data in a plurality of predetermined performance intensity zones, wherein each performance intensity zone comprises a predetermined first numerical range for the first activity and a predetermined second numerical range for the second activity, the predetermined first numerical range and the predetermined second numerical range being based on a first maximum heart rate associated with the user,
    wherein the first activity and the second activity are at least one of different types of sports and different types of physical activities,
    wherein the predetermined first numerical range and the second predetermined numerical range are represented with a same specific unit of measure, the predetermined first numerical range being different from the predetermined second numerical range, the one or more memories further storing instructions, that, when executed by the one or more processors, cause the apparatus to output the performance intensity data with the same specific unit of measure for the first activity and the second activity.

2. The apparatus of claim 1, wherein the first numerical range and the second numerical range are presented by heart rate values, the operations further comprising at least one of the following operations:
    obtaining the first maximum heart rate in the first activity predetermining the performance intensity zone in the first numerical range for the first activity using a first predetermined relationship associated with the first maximum heart rate, and predetermining the performance intensity zone in the second numerical range for the second activity using a second predetermined relationship associated with the first maximum heart rate;
    obtaining the first maximum heart rate in the first activity and a rest heart rate, predetermining the performance intensity zone in the first numerical range for the first activity using a third predetermined relationship associated with the first maximum heart rate and the rest heart rate, and predetermining the performance intensity zone in the second numerical range for the second activity using a fourth predetermined relationship associated with the first maximum heart rate and the rest heart rate; and
    obtaining a first training time of the first activity and a second training time of the second activity from an analysis of the performance intensity data, adjusting the first numerical range on the basis of the first training time of the first activity, and adjusting the second numerical range on the basis of the second training time of the second activity.

3. The apparatus of claim 1, further comprising at least one input interface for the one or more measurement sensors, the one or more measurement sensors comprising at least one of the following: a heart rate sensor, a motion sensor, a location sensor, a bike sensor.

4. The apparatus of claim 1, wherein the one or more measurement sensors comprise a first input interface for a first measurement sensor for measuring the first activity, a second input interface for a second measurement sensor for measuring the second activity, the first measurement sensor and the second measurement sensor being selected from a heart rate sensor, a motion sensor, a location sensor, and a bike sensor such that the first measurement sensor is not of the same type as the second measurement sensor.

5. The apparatus of claim 1, wherein the apparatus comprises at least one of the following: a wrist-worn sports computer, a bicycle computer, a mobile phone, a tablet pc, a portable computer, a computer, a server computer, a server computer accessible over a data network.

6. An apparatus comprising,
    one or more processors;
    one or measurement sensors operatively coupled to the one or more processors; and
    one or more memories storing instructions that, when executed by the one or more processors, cause the apparatus to perform operations comprising:
    obtaining performance intensity data measured from a user, using the one or more measurement sensors, during at least one of a first activity and a second activity; and
    classifying the performance intensity data in a plurality of predetermined performance intensity zones, wherein each performance intensity zone comprises a predetermined first numerical range for the first activity and a predetermined second numerical range for the second activity, the predetermined first numerical range and the predetermined second numerical range being based on a first maximum heart rate associated with the user, wherein the first activity and the second activity are at least one of different types of sports and different types of physical activities, wherein the predetermined first numerical range is represented with a first unit of measure, the predetermined second numerical range is represented with a second unit of measure, the predetermined first numerical range being different from the predetermined second numerical range, the operations further comprising outputting the performance intensity data in an arbitrary unit of measure, which is different from the first unit of measure and the second unit of measure.

7. A method comprising:

obtaining performance intensity data measured from a user, using one or more measurement sensors operatively coupled to one or more processors, during at least one of a first activity and a second activity; and classifying the performance intensity data in a plurality of predetermined performance intensity zones, wherein each performance intensity zone comprises a predetermined first numerical range for the first activity and a predetermined second numerical range for the second activity, the predetermined first numerical range and the predetermined second numerical range being based on a first maximum heart rate associated with the user, wherein the first activity and the second activity are at least one of different types of sports and different types of physical activities, wherein the predetermined first numerical range and the predetermined second numerical range are represented with a same specific unit of measure, the predetermined first numerical range being different from the predetermined second numerical range, the operations further comprising outputting the performance intensity data with the same specific unit of measure for the first activity and the second activity.

8. The method of claim 7, wherein the first numerical range and the second numerical range are presented by heart rate values, and the method comprises at least one of:

obtaining the first maximum heart rate in the first activity, predetermining the performance intensity zone in the first numerical range for the first activity using a first predetermined relationship associated with the first maximum heart rate, and predetermining the performance intensity zone in the second numerical range for the second activity using a second predetermined relationship associated with the first maximum heart rate;

obtaining the first maximum heart rate in the first activity and a rest heart rate, predetermining the performance intensity zone in the first numerical range for the first activity using a third predetermined relationship associated with the first maximum heart rate and the rest heart rate, and predetermining the performance intensity zone in the second numerical range for the second activity as a fourth predetermined relationship associated with the first maximum heart rate and the rest heart rate; and obtaining a first training time of the first activity and a second training time of the second activity from an analysis of the performance intensity data, adjusting the first numerical range on the basis of the first training time of the first activity, and adjusting the second numerical range on the basis of the second training time of the second activity.

9. The method of claim 7, further comprising measuring the performance intensity data from the user with the one or more measurement sensors during the first activity and/or the second activity, the one or more measurement sensors comprising at least one of the following: a heart rate sensor, a motion sensor, a location sensor, a bike sensor.

10. The method of claim 7, further comprising measuring the first activity with a first measurement sensor and the second activity with a second measurement sensor, the first measurement sensor and the second measurement sensor being selected from a heart rate sensor, a motion sensor, a location sensor, and a bike sensor such that the first measurement sensor is not of the same type as the second measurement sensor.

11. A method comprising:

obtaining performance intensity data measured from a user, using one or more measurement sensors operatively coupled to one or more processors, during at least one of a first activity and a second activity; and classifying the performance intensity data in a plurality of predetermined performance intensity zones, wherein each performance intensity zone comprises a predetermined first numerical range for the first activity and a predetermined second numerical range for the second activity, the predetermined first numerical range and the predetermined second numerical range being based on a first maximum heart rate associated with the user, wherein the first activity and the second activity are at least one of different types of sports and different types of physical activities, wherein the predetermined first numerical range is represented with a first unit of measure, the predetermined second numerical range is represented with a second unit of measure, and the first unit of measure is different from the second unit of measure, the predetermined first numerical range being different from the predetermined second numerical range, the method further comprising outputting the performance intensity data in an arbitrary unit of measure, which is different from the first unit of measure and the second unit of measure.

12. A non-transitory computer-readable medium comprising instructions which, when executed by an apparatus, cause the apparatus to perform operations comprising:

obtaining performance intensity data measured from a user ,using one or more measurement sensors operatively coupled to one or more processors, during at least one of a first activity and a second activity; and classifying the performance intensity data in a plurality of predetermined performance intensity zones, wherein each performance intensity zone comprises a predetermined first numerical range for the first activity and a predetermined second numerical range for the second activity, the predetermined first numerical range and the predetermined second numerical range being based on a first maximum heart rate associated with the user, wherein the first activity and the second activity are at least one of different types of sports and different types of physical activities, wherein the predetermined first numerical range and the predetermined second numerical range are represented with a same specific unit of measure, the predetermined first numerical range being different from the predetermined second numerical range, the operations further comprising outputting the performance intensity data with the same specific unit of measure for the first activity and the second activity.

* * * * *